United States Patent
Pagonis et al.

(10) Patent No.: US 10,820,962 B2
(45) Date of Patent: Nov. 3, 2020

(54) SURGICAL OPTICAL SYSTEM WITH HEADS UP DISPLAY

(71) Applicants: TSME, LLC, Windham, NH (US); Simon Beylin, Upton, MA (US)

(72) Inventors: Tom C. Pagonis, Chestnut Hill, MA (US); Simon Beylin, Upton, MA (US); Michael J. Kang, Seattle, WA (US); Eric W. Young, Granite Bay, CA (US)

(73) Assignee: TSME, LLC, Windham, NH (US)

( * ) Notice: Subject to any disclaimer, the term of this patent is extended or adjusted under 35 U.S.C. 154(b) by 82 days.

(21) Appl. No.: 15/870,424

(22) Filed: Jan. 12, 2018

(65) Prior Publication Data

US 2018/0235723 A1 Aug. 23, 2018

Related U.S. Application Data

(63) Continuation of application No. PCT/US2016/042252, filed on Jul. 14, 2016.
(Continued)

(51) Int. Cl.
| | |
|---|---|
| *A61B 90/20* | (2016.01) |
| *G02B 21/20* | (2006.01) |
| *A61B 90/00* | (2016.01) |
| *G02B 21/36* | (2006.01) |
| *A61B 1/24* | (2006.01) |
| *A61B 5/00* | (2006.01) |
| *A61B 5/01* | (2006.01) |

(Continued)

(52) U.S. Cl.
CPC ............... *A61B 90/37* (2016.02); *A61B 1/24* (2013.01); *A61B 5/0077* (2013.01); *A61B 5/01* (2013.01); *A61B 5/021* (2013.01); *A61B 6/032* (2013.01); *A61B 6/5294* (2013.01); *A61B 90/20* (2016.02); *A61B 90/361* (2016.02); *G02B 21/0012* (2013.01); *G02B 21/20* (2013.01); *G02B 21/361* (2013.01); *G02B 21/364* (2013.01); *G02B 21/365* (2013.01); *G06F 3/14* (2013.01); *G06T 7/0012* (2013.01); *A61B 5/7425* (2013.01); *A61B 2090/372* (2016.02); *A61B 2090/373* (2016.02); *A61B 2090/3762* (2016.02); *G06T 2207/10081* (2013.01)

(58) Field of Classification Search
CPC ............ G02B 2027/0138; G02B 23/18; G02B 27/0172; A61B 3/14
See application file for complete search history.

(56) References Cited

U.S. PATENT DOCUMENTS

| | | |
|---|---|---|
| 5,235,457 A | 8/1993 | Lichtman et al. |
| 5,239,984 A | 8/1993 | Cane et al. |
| | (Continued) | |

OTHER PUBLICATIONS

International Search Report and Written Opinion for Application No. PCT/US2016/042252, dated Nov. 29, 2016. 22 pages.

*Primary Examiner* — Obafemi O Sosanya
(74) *Attorney, Agent, or Firm* — McCarter & English, LLP; Jonathan M. Sparks

(57) ABSTRACT

Methods and systems are provided herein for a surgical optical system having a heads up display including, in accordance with various embodiments, an optical device, an image sensor optically coupled to the optical device to acquire image data from a field of view of the optical device, and a display device configured to display an acquired image representing the image data acquired by the image sensor.

11 Claims, 9 Drawing Sheets

Related U.S. Application Data

(60) Provisional application No. 62/192,351, filed on Jul. 14, 2015.

(51) Int. Cl.
|  |  |
|---|---|
| *A61B 5/021* | (2006.01) |
| *A61B 6/03* | (2006.01) |
| *A61B 6/00* | (2006.01) |
| *G02B 21/00* | (2006.01) |
| *G06F 3/14* | (2006.01) |
| *G06T 7/00* | (2017.01) |

(56) References Cited

U.S. PATENT DOCUMENTS

| | | |
|---|---|---|
| 5,608,210 A | 3/1997 | Esparza et al. |
| 5,662,111 A * | 9/1997 | Cosman ............... G06K 9/28 600/417 |
| 2004/0224279 A1 | 11/2004 | Siemons |
| 2010/0182418 A1 | 7/2010 | Jess et al. |
| 2010/0324366 A1 | 12/2010 | Shimotsu |
| 2011/0228906 A1 | 9/2011 | Jaffray et al. |
| 2012/0300050 A1 | 11/2012 | Korichi et al. |
| 2013/0100271 A1 | 4/2013 | Howes |
| 2013/0253335 A1 | 9/2013 | Noto et al. |
| 2014/0092460 A1 | 4/2014 | Schwedt et al. |
| 2015/0269777 A1 * | 9/2015 | Sax ....................... G02B 23/18 345/633 |
| 2015/0371390 A1 | 12/2015 | Gassner et al. |

* cited by examiner

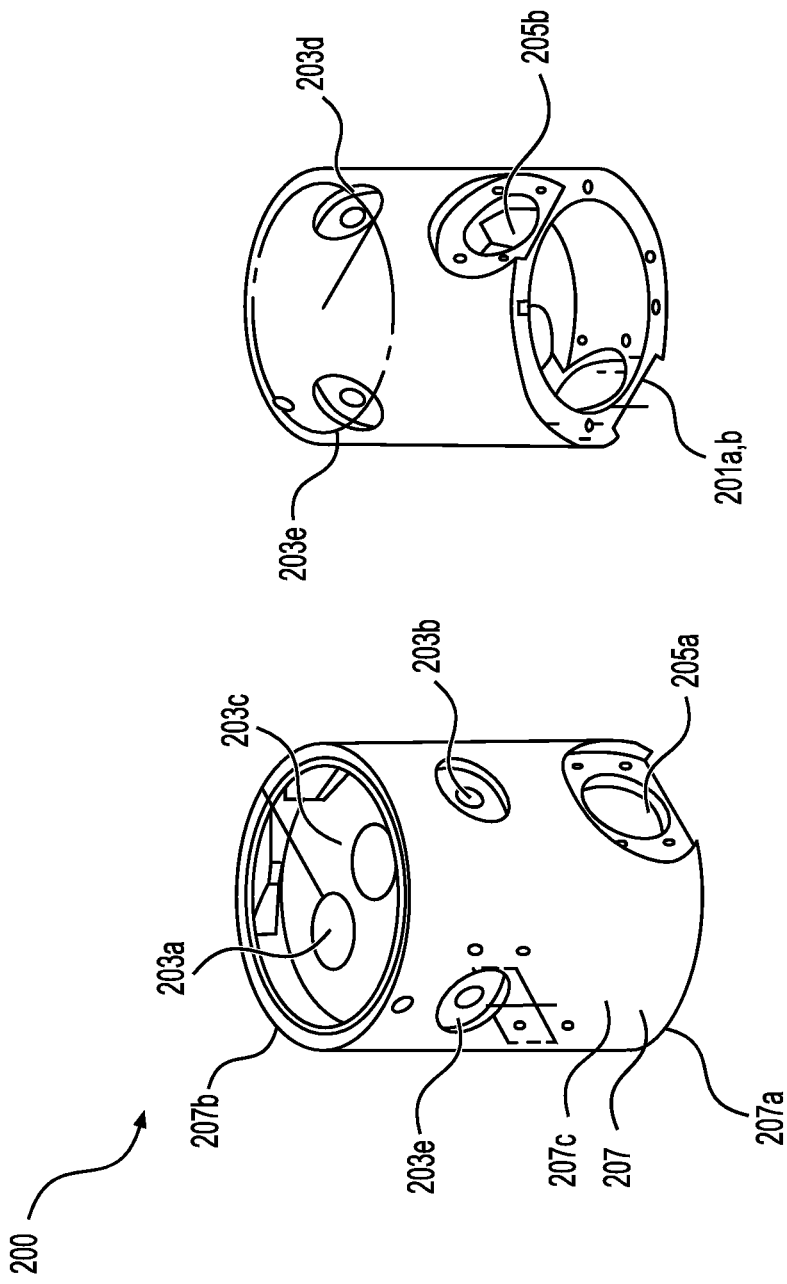

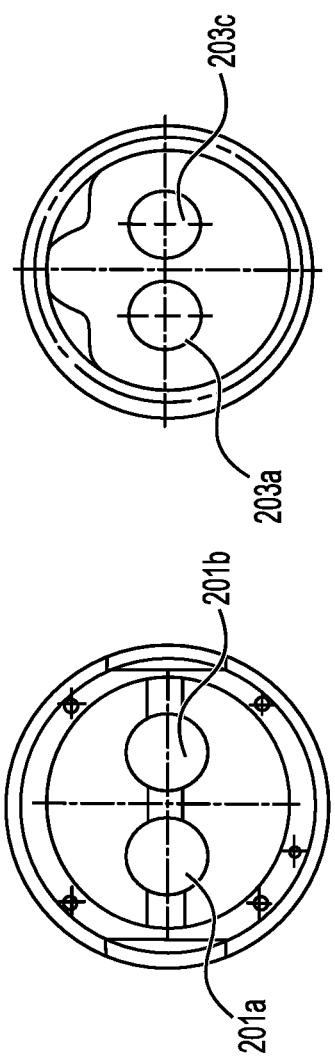

SURGICAL OPTICAL SYSTEM WITH HEADS UP DISPLAY

RELATED APPLICATIONS

This application is a continuation of International Application No. PCT/US2016/042252, filed Jul. 14, 2016, which claims the benefit of U.S. Provisional Application No. 62/192,351, filed Jul. 14, 2015. The entire contents of each of the above documents is herein incorporated by reference in their entirety.

FIELD OF INVENTION

The disclosure relates generally to microscope systems and more particularly to dental microscopes having a heads up display.

BACKGROUND

Conventionally, microscopes such as dental, surgical, clinical, pathological, or laboratory microscopes include only a traditional eyepiece, requiring the user to assume an ergonomically undesirable hunched position while using the microscope and inducing eyestrain. As a result, for example, dental practitioners experience fatigue and high rates of ergonomic injury. Furthermore, the user must look away from the eyepiece in order to check important procedure-related information such as instrument status, patient condition, radiographs, clinical or pathological data, procedural instructions, etc., thereby increasing procedure time, thereby exacerbating the ergonomic issues described above, creating lower patient or sample throughput, and, in dental/surgical applications, potentially increasing the amount of anesthesia and/or anesthetic required during the procedure.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2A is an isometric view of an exemplary beam splitting device in accordance with various embodiments.

FIG. 2B is an isometric view of an interior of an exemplary beam splitting device in accordance with various embodiments.

FIG. 2C is a bottom view of an exemplary beam splitting device in accordance with various embodiments.

FIG. 2D is a first side view of an exemplary beam splitting device in accordance with various embodiments.

DETAILED DESCRIPTION

Figure 1:
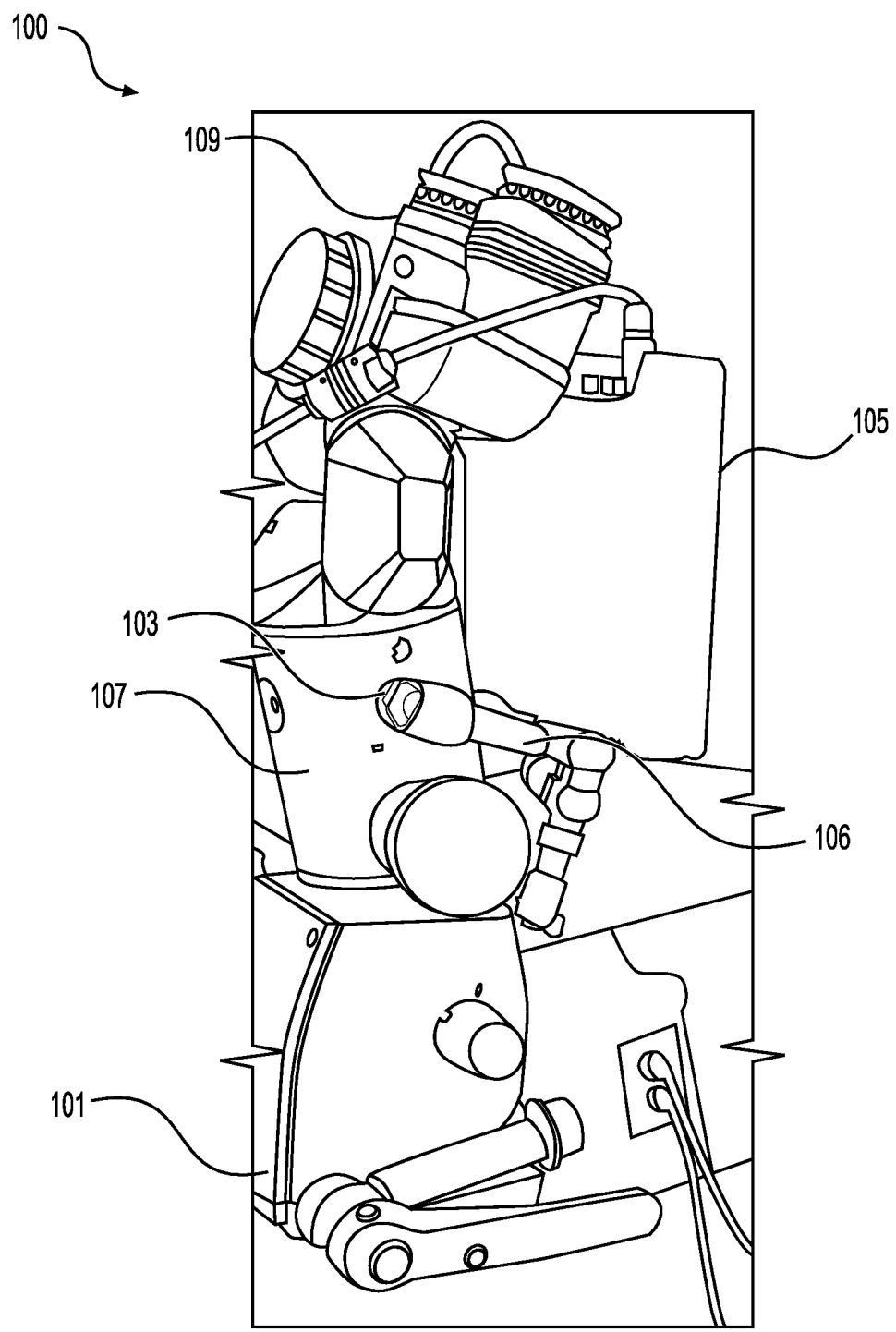
FIG. 1 is a side view of an exemplary microscope system in accordance with various embodiments.

As discussed above, conventional dental and surgical microscopes include only a traditional eyepiece, requiring the practitioner to remain in an ergonomically undesirable hunched position while performing a procedure. As a result, dental practitioners experience fatigue and high rates of ergonomic injury. Furthermore, the practitioner must look away from the eyepiece in order to check important procedure-related information such as instrument status, patient condition, radiographs, etc., thereby increasing procedure time, thereby exacerbating the ergonomic issues described above, creating lower patient throughput, and potentially increasing the amount of anesthesia and/or anesthetic required during the procedure.

Methods and systems are provided herein for a surgical optical system having a heads up display including, in accordance with various embodiments, an optical device, an image sensor optically coupled to the optical device to acquire image data from a field of view of the optical device, and a display device configured to display an acquired image representing the image data acquired by the image sensor.

Referring now to FIGS. 1 and 2A-G, an exemplary retrofitted or converted surgical microscope 100 includes an objective 101 having a field of view, a beam splitter 107 (e.g., within a beam splitting apparatus 200 as shown) for splitting an optical input received from the objective 101, an eyepiece 109 optically coupled to a first split beam path (e.g., first optical output 203a as shown in FIGS. 2A-G) of the beam splitter 107 (or, for a bifocal eyepiece as shown, the eyepiece can be optically coupled to each of two distinct split beam paths (e.g., first optical output 203a and third optical output path 203c as shown in FIGS. 2A-G) of the beam splitter 107), an image sensor 103 optically coupled to a second split beam path (e.g., second optical output path 203b as shown in FIGS. 2A-G) of the beam splitter 107 to acquire image data, and a display device 105 in electrical communication with the image sensor for displaying an acquired image representing the image data received from the image sensor 103.

Objective 101, in accordance with various embodiments, can include but is not limited to, any suitable objective configuration, including, for example but not limited to, a single lens, a multi-element compound lens, or an oil immersion lens. The objective 101, in accordance with various embodiments, can be designed for any suitable level of magnification in combination with any suitable numerical aperture.

Image sensor 103, in accordance with various embodiments, can include but is not limited to, video sensors, any focal plane array/staring array, charge coupled device (CCD) sensors, complimentary metal-oxide-semiconductor (CMOS) sensors, back-side illuminated CMOS sensors, hybrid CCD/CMOS (sCMOS) sensors, N-type metal-oxide-semiconductor (NMOS) sensors, specialty sensors, curved sensors, or any other suitable image sensing device. In accordance with various embodiments, a camera adapter (not shown) can be interposed between the objective 101 and the image sensor 103 for providing focus, iris, zoom, and aperture control functionality.

Display device 105, in accordance with various embodiments, can include but is not limited to, a computer monitor, a television, a touchscreen monitor, a screen of a mobile device (such as but not limited to, a smartphone, a tablet, or an electronic book), and/or any other display device that can be used for displaying an image and/or video representing image data. In accordance with various embodiments, such as but not limited to where the display device 105 is a touchscreen or a display of a mobile device, the display device 105 can also double as an input device for receiving user input. In accordance with various embodiments, the display device 105 can be configured to directly receive image data or other input via an integral processor. In accordance with various embodiments, the display device can be configured to receive image data or other input via one or more intermediary processing devices such as a computer or tablet, a surgical instrument monitor, a patient data store. In some embodiments, display device 105 can be mounted via a movable mount (e.g., a gimbal, an articulating arm, a hinge, or any other suitable movable mount) for repositioning the display relative to the objective 101. Such repositioning advantageously allows a user to achieve better ergonomic position during use and/or to enable shared viewing with other members of the surgical team.

Beam splitter 107, in accordance with various embodiments, can include but is not limited to, one or more of a polarizing beam splitter, non-polarizing beam splitter, Wollaston prism, pellicle beam splitter, dichroic beam splitter, mirror-type beam splitter, plate beam splitter, cube beam splitter, polka dot beam splitter, Brewster window, variable beam splitter, or a wedged beam splitter. The beam splitter 107 can divide a light beam of the objective 101 in any suitable ratio including, for example but not limited to, 50:50, 80:20, 70:30, 95:5, or any other desired ratio.

Figure 2G:
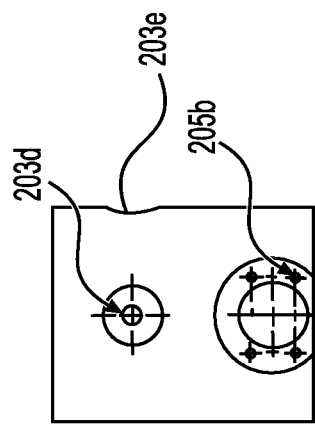
FIG. 2G is a third side view of an exemplary beam splitting device in accordance with various embodiments.
Figure 2F:
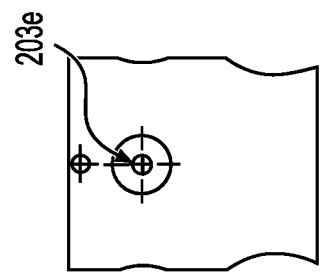
FIG. 2F is a second side view of an exemplary beam splitting device in accordance with various embodiments.
Figure 2E:
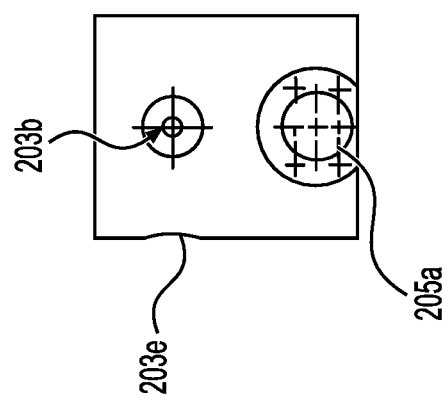
FIG. 2E is a rear view of an exemplary beam splitting device in accordance with various embodiments.

In accordance with various embodiments, beam splitter 107 is positioned within a beam splitting apparatus 200. Referring now to FIGS. 2A-G, the beam splitting apparatus 200, in accordance with various embodiments, includes a housing 207 defining an interior volume, one or more beam splitters 107 (not shown) being positioned within the interior volume. The housing 207 includes a first surface 207a, a second surface 207b, and a third surface 207c. The first surface 207a of the beam splitting apparatus 200, in accordance with various embodiments, defines at least one optical input path 201a, 201b for receiving an optical input from the objective lens 101. For example, as shown in FIG. 2B, to optical input paths 201a, 201b are defined to provide a binocular optical input. When an optical input is received through the optical input path 201a, 201b, the input is then split within the beam splitting apparatus by the beam splitter(s) 107 into at least first and second optical outputs, although it will be apparent in view of this disclosure that splitting the optical input into third, fourth, fifth, or any number of additional optical outputs is contemplated in accordance with various embodiments. For example, as shown in FIGS. 2A-G, the beam splitting apparatus 200 includes five optical outputs 203a, 203b, 203c, 203d, 203e. The second surface 207b of the beam splitting apparatus 200 defines at least a first optical output path 203a, 203c for emitting the first optical output and the third surface 207c of the beam splitting apparatus 200 defines at least a second optical output path 203b, 203d, 203e for emitting the second optical output. As shown in FIGS. 1 and 2A-G, first 203a and third 203c optical outputs are defined in the second surface 207b for providing a binocular output to a binocular eyepiece (e.g., eyepiece 109 as shown in FIG. 1) and second 203b, fourth 203d, and fifth 203e optical outputs are defined in the third surface 207c for providing optical output to one or more image sensors, additional eyepieces, or other devices. Although a single image sensor 103 is shown attached to the second optical output 203b in FIG. 1, it will be apparent in view of this disclosure that one or more additional image sensors may be desirable in accordance with various embodiments. For example, in some embodiments, an additional image sensor (not shown) can be optically coupled to the fourth or fifth optical output to provide acquired image data to an additional display (not shown) for use by a surgical assistant or other interested party. In some embodiments, an additional image sensor (not shown) can be optically coupled to the fourth or fifth optical output to provide acquired image data to a recording device for providing raw footage of the surgery (e.g., for training purposes). In accordance with various embodiments, the beam splitting apparatus 200 also includes one or more mounting attachments 205a, 205b for mounting the beam splitting apparatus 200 to an optical device (e.g., a surgical microscope as shown in FIG. 1).

Eyepiece 109, in accordance with various embodiments, can include but is not limited to, one or more of a monocular eyepiece, a binocular eyepiece, a single lens eyepiece, a compound lens eyepiece, a Galilean lens, a convex lens, a Huygens eyepiece, a Ramsden eyepiece, a Kellner eyepiece, a symmetrical eyepiece, an orthoscopic eyepiece, a monocentric eyepiece, an Erfle eyepiece, a Konig eyepiece, an RKE eyepiece, or a Nagler eyepiece.

Figure 3:
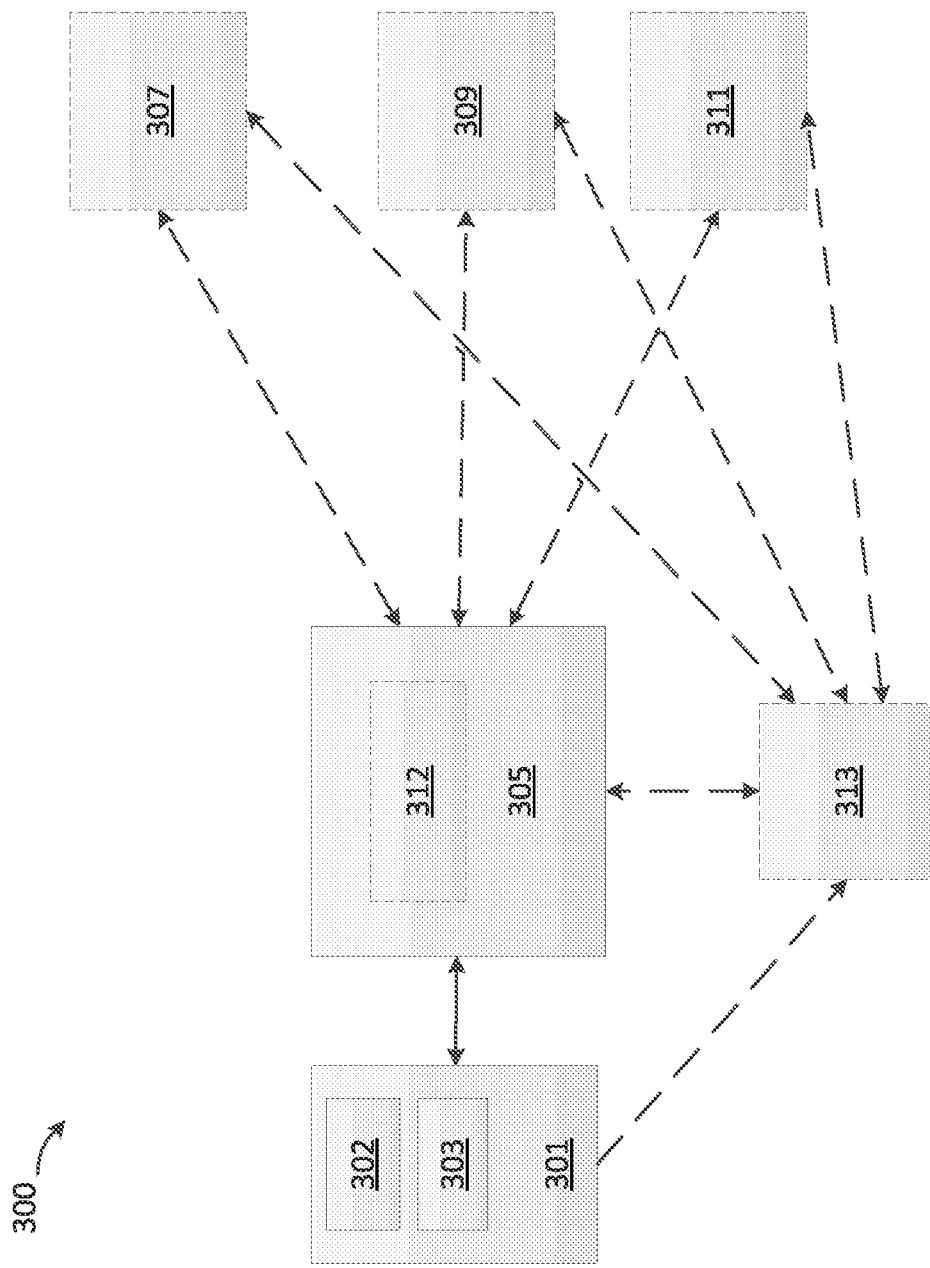
FIG. 3 is a block diagram representing an exemplary surgical optical system in accordance with various embodiments.

Referring now to FIG. 3, a surgical optical system 300 can include a visual monitoring component 301 including an optical device 302 having a field of view and an image sensor 303 optically coupled to the optical device 302 for acquiring image data from the field of view of the optical deivce 302. The surgical optical system 300 also includes a display 305 for displaying acquired images such as, for example, still photographs, video, etc., from the image sensor 303. The system 300, in accordance with various embodiments, can include one or more processing devices 312, 313 (e.g., an integral processor of the display or an external processing or computing device). The processing device 312, 313, in accordance with various embodiments, can be configured to receive surgical instrument data from one or more surgical instruments 307 and to instruct the display 305 or an additional display (not shown) to render the received surgical instrument data. The processing device 312, 313, in accordance with various embodiments, can be configured to receive patient data from a patient monitoring system 309 or a patient data store 311 and to instruct the display 305 or an additional display (not shown) to render the received patient data. Although shown herein as including one image sensor 303, it will be apparent in view of this disclosure that, in accordance with various embodiments, the visual monitoring component can also include one or more additional optical devices, image sensors, displays, or data inputs.

Optical devices 302 can be any suitable optical lens or set of lenses arranged to have a field of view (FOV) including, for example but not limited to, a microscope, a dental microscope, a surgical microscope, an endoscope, an exoscope, a loupe, a magnifying glass, an eyepiece, an objective, a binocular, a telescope, a camera, and any combinations thereof. Optical sensors 303 can include, for example but not limited to, video sensors, any focal plane array/ staring array, charge coupled device (CCD) sensors, complimentary metal-oxide-semiconductor (CMOS) sensors, back-side illuminated CMOS sensors, hybrid CCD/CMOS (sCMOS) sensors, N-type metal-oxide-semiconductor (NMOS) sensors, specialty sensors, curved sensors, or any other suitable image sensing device. One or more image sensors 303 can be coupled to the optical device 302 for acquiring image data from the FOV of the optical device 302. In some embodiments, an image sensor 303 can be positioned directly within an optical path of the optical device 302. In some embodiments, a beam splitter (e.g., 107, 200 as shown in FIGS. 1-2G) can be interposed between the image sensor 303 and the optical path of the optical device 302 for providing optical image data to the image sensor 303 and at least one other device (e.g., an eyepiece or additional image sensor). In some embodiments, optical devices 302 can also include a camera adapter or similar functionality interposed between the FOV and the image sensor 303 for providing focus, iris, zoom, and aperture control functionality.

Display 305 is configured to receive and display the optical image data acquired by the one or more image sensors 303. Display 305 can include, for example but not limited to, a computer monitor, a television, a touchscreen monitor, a screen of a mobile device (such as but not limited to, a smartphone, a tablet, or an electronic book), and/or any other display device that can be used for displaying an image and/or video representing image data. The display 305 can receive the image data directly from the image sensor 303 or can receive the image data via one or more internal processing devices 312 or external processing devices 313. The processing devices 312, 313 can include, for example but not limited to general or special purpose processors, microprocessors, field programmable gate arrays (FPGA), multi-core processors, or any other suitable processing device. In some embodiments, display 305 receives the optical image data via one or more electronic signal splitting devices (not shown). Electronic signal splitting devices can include, for example but not limited to, coaxial splitters, HDMI splitters, digital signal processors, combinations thereof, or any other suitable electronic signal splitting device.

In accordance with various embodiments, the display 305 or the processing device(s) can be configured to receive and display other external data alongside or overlaid on the rendered image data. For example, in some embodiments, the display can be configured to receive surgical instrument data from one or more surgical instruments 307. Surgical instrument data can include, for example, any relevant data, including for example, torque, revolutions per minute, pneumatic pressure, temperature, attachment wear, quantity of medication/anesthesia delivered, or combinations thereof. In some embodiments, the display can be configured to receive patient data from one or more patient monitoring systems 309 or patient data stores 311. Patient data received from a patient monitoring system can include, for example, heart rate, body temperature, or blood pressure. Patient data received from a patient data store 311 can include, for example, radiographs, computed cone beam computed tomography images, photographs, medical (including dental) history, or personal data (e.g., name, address, insurance information, date of birth). Such external data can, in accordance with various embodiments, be displayed contemporaneously on a segregated portion of the display 305, can temporarily replace the rendered image on the display 305, can be overlaid on the rendered image on the display 305, be displayed on one or more additional displays, or be presented in any other suitable configuration. In some embodiments, the display 305 or processor(s) 312, 313 can also be configured to receive and display appointment or other non-patient data (e.g., an appointment schedule calendar).

Where the patient data includes cone beam computed tomography (CBCT) images, the surgical optical system 300 can be configured to, by the processing device(s) 312, 313, align the CBCT image with the acquired image from the image sensor 303 and instruct the display 305 to overlay the displayed acquired image with the CBCT image. In some embodiments, the surgical optical system 300 can be configured to identify, by the processing device(s) 312, 313, areas of interest within the overlaid image and instruct the display 305 to render visual indicators at the locations of interest within the displayed acquired image. In some embodiments, the surgical optical system 300 can be configured to identify, by the processing device(s) 312, 313, one or more sectioning planes based on the computed cone beam tomography image and instruct the display 305 to render visual representations of the sectioning planes within the displayed acquired image.

It will be apparent in view of this disclosure that the display 305 can be interactive (e.g., via a touchscreen input, keyboard/mouse control, and/or any other suitable means) and thereby allow the user to, for example, zoom in and out, adjust focus, adjust aperture, query displayed data, freeze, rewind, or otherwise control video, etc. In accordance with various embodiments, the display 305 or the processing device(s) 312, 313 can be configured to receive audio data (e.g., via a microphone) and/or produce sound (e.g., via built in or external speakers). In some embodiments, audio capability can be used to produce a warning signal (e.g., if a surgical instrument fails, needs to be replaced, or exceeds an operational threshold or if monitored patient data exceeds a preset limit).

In some embodiments, audio capability can be used to allow the user to make audio, audio/video, or "intercom" calls to consult with colleagues or staff. In some embodiments, audio capability can be used to play music or other media content during use. In some embodiments, the audio capability can provide voice command capability such as, for example, search functionality (e.g., of patient data, patient electronic charts, instrument data, procedural guidelines, a secure cloud account, the internet, or any other searchable electronic information), display control functionality (e.g., content and configuration of the display), optical control functionality (e.g., zoom, focus, aperture, magnification level, or other optical controls), and communication functionality (e.g., file transfers, uploads, downloads, email, instant message, voice calls, video calls, or any other form of electronic communication). In some embodiments, audio capability can be used to allow the user to create and store audio or audio/video files (e.g., narrated notes or a recording of the displayed image data). In some embodiments, the audio or video files can be associated with a particular record or file (e.g., a patient record, a patient radiograph, a video of the procedure, or any other record or file). Similarly, the audio capability can allow the user to play audio, audio/video, or other audible media content accessed or created as described above.

Figure 4:
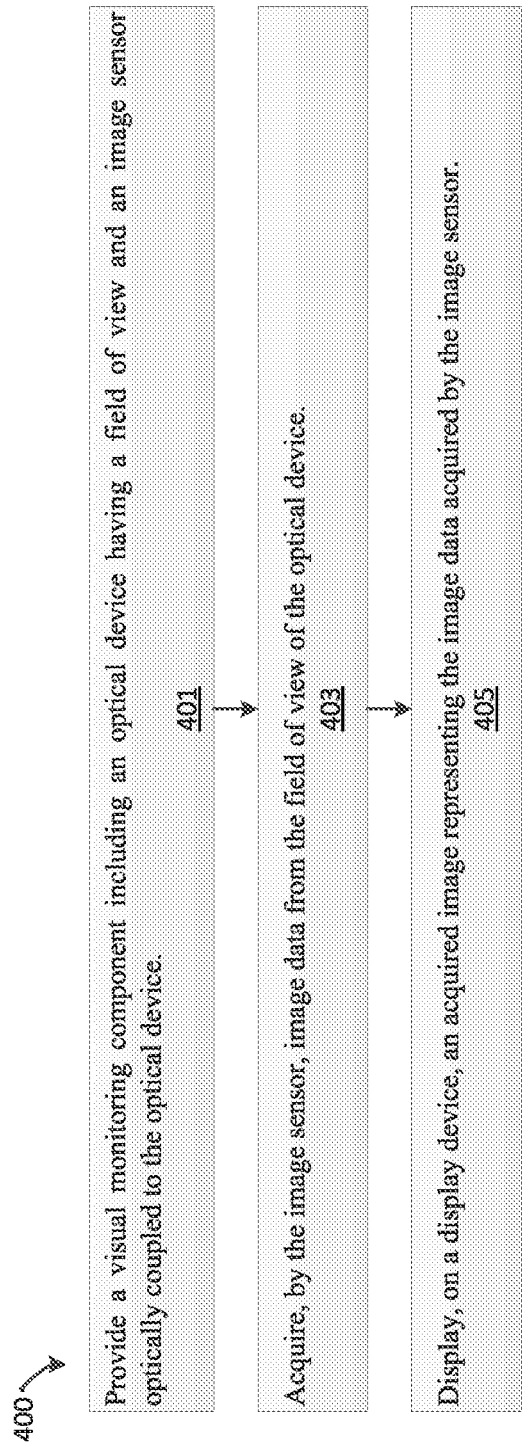
FIG. 4 is a flow diagram illustrating an exemplary method for operating a surgical optical system in accordance with various embodiments.

Referring now to FIG. 4, a method is provided for operating a surgical system. The method includes the step of providing a visual monitoring component including an optical device having a field of view and an image sensor optically coupled to the optical device 401. The method also includes the step of acquiring, by the image sensor, image data from the field of view of the optical device 403. The method also includes displaying, on a display device, an acquired image representing the image data acquired by the image sensor 405.

The step of providing a visual monitoring component including an optical device having a field of view and an image sensor optically coupled to the optical device 401 can be performed, for example but not limited to, by providing an optical device 302 and an image sensor 303 as described above with reference to FIG. 3 or a converted surgical microscope 100 including an objective 101, a beam splitter 107, and an image sensor 103 as described above with reference to FIG. 1.

The step of acquiring, by the image sensor, image data from the field of view of the optical device 403 can be performed, for example but not limited to, using an image sensor 103, 303 as described above with reference to FIGS. 1 and 3.

The step of displaying, on a display device, an acquired image representing the image data acquired by the image sensor 405 can be performed, for example but not limited to, using display 105, 305, image sensor 103, 303, and/or processor 312, 313 as described above with reference to FIGS. 1 and 3.

Figure 5:
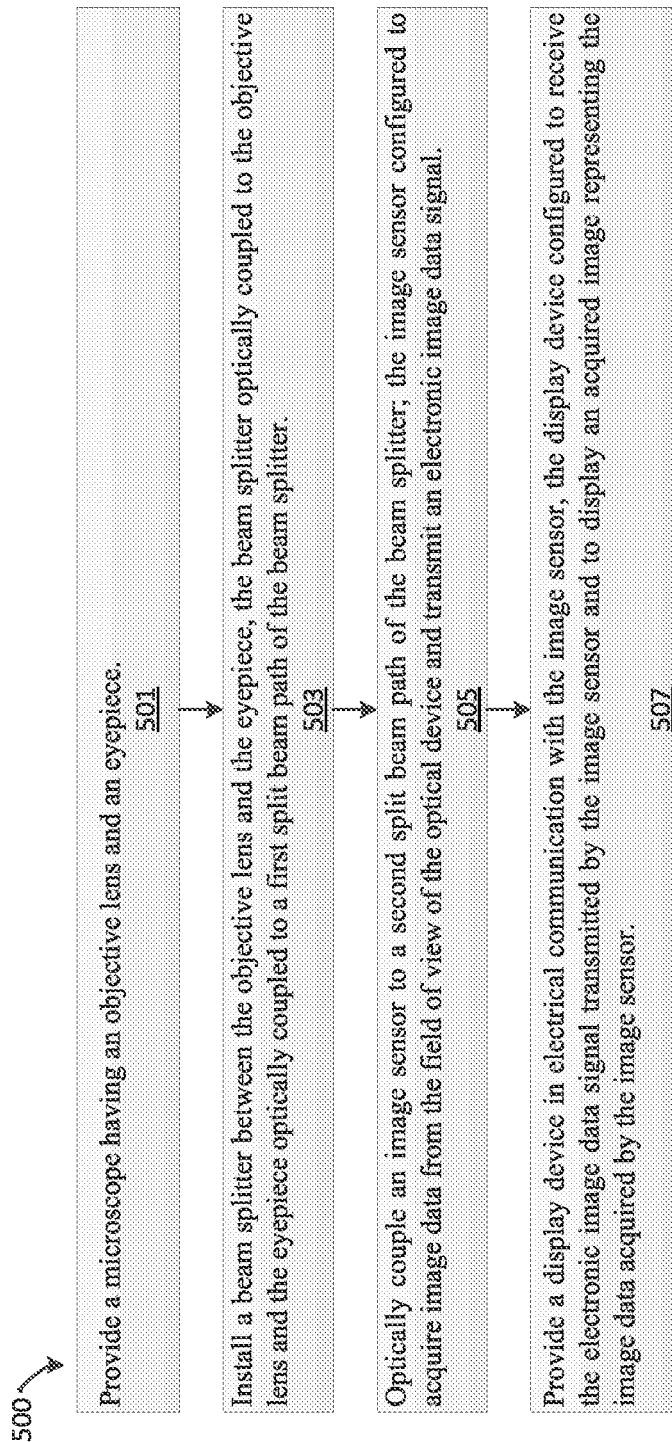
FIG. 5 is a flow diagram illustrating an exemplary method for converting a microscope to a surgical system in accordance with various embodiments.

Referring now to FIG. 5, a method is provided for converting a microscope to a surgical system. The method includes the step of providing a microscope having an objective lens and an eyepiece 501. The method also includes the step of installing a beam splitter between the objective lens and the eyepiece, the beam splitter optically coupled to the objective lens and the eyepiece optically coupled to a first split beam path of the beam splitter 503. The method also includes optically coupling an image sensor to a second split beam path of the beam splitter; the image sensor configured to acquire image data from the field of view of the optical device and transmit an electronic image data signal 505. The method also includes providing a display device in electrical communication with the image sensor, the display device configured to receive the electronic image data signal transmitted by the image sensor and to display an acquired image representing the image data acquired by the image sensor 507.

The step of providing a microscope having an objective lens and an eyepiece 501 can be performed, for example but not limited to, by providing a microscope having an objective 101 and an eyepiece 109 as described above with reference to FIG. 1.

The step of installing a beam splitter between the objective lens and the eyepiece, the beam splitter optically coupled to the objective lens and the eyepiece optically coupled to a first split beam path of the beam splitter 503 can be performed, for example but not limited to, by installing a beam splitter 107 or beam splitting apparatus 200 as described above with reference to FIGS. 1 and 2.

The step of optically coupling an image sensor to a second split beam path of the beam splitter; the image sensor configured to acquire image data from the field of view of the optical device and transmit an electronic image data signal 505 can be performed, for example but not limited to, optically coupling image sensor 103 to beam splitter 107 as described above with reference to FIG. 1.

The step of providing a display device in electrical communication with the image sensor, the display device configured to receive the electronic image data signal transmitted by the image sensor and to display an acquired image representing the image data acquired by the image sensor 507 can be performed, for example but not limited to, using image sensor 103, 303 and display device 105, 305 as described above with reference to FIGS. 1 and 3. In some embodiments, the display device can be mounted via a movable mount (e.g., a gimbal, an articulating arm, a hinge, or any other suitable movable mount) for repositioning the display relative to other components of the microscope. As discussed above, such repositioning advantageously allows a user to achieve better ergonomic position during use and/or to enable shared viewing with other members of the surgical team.

Non-Limiting Example Computing Devices

Figure 6:
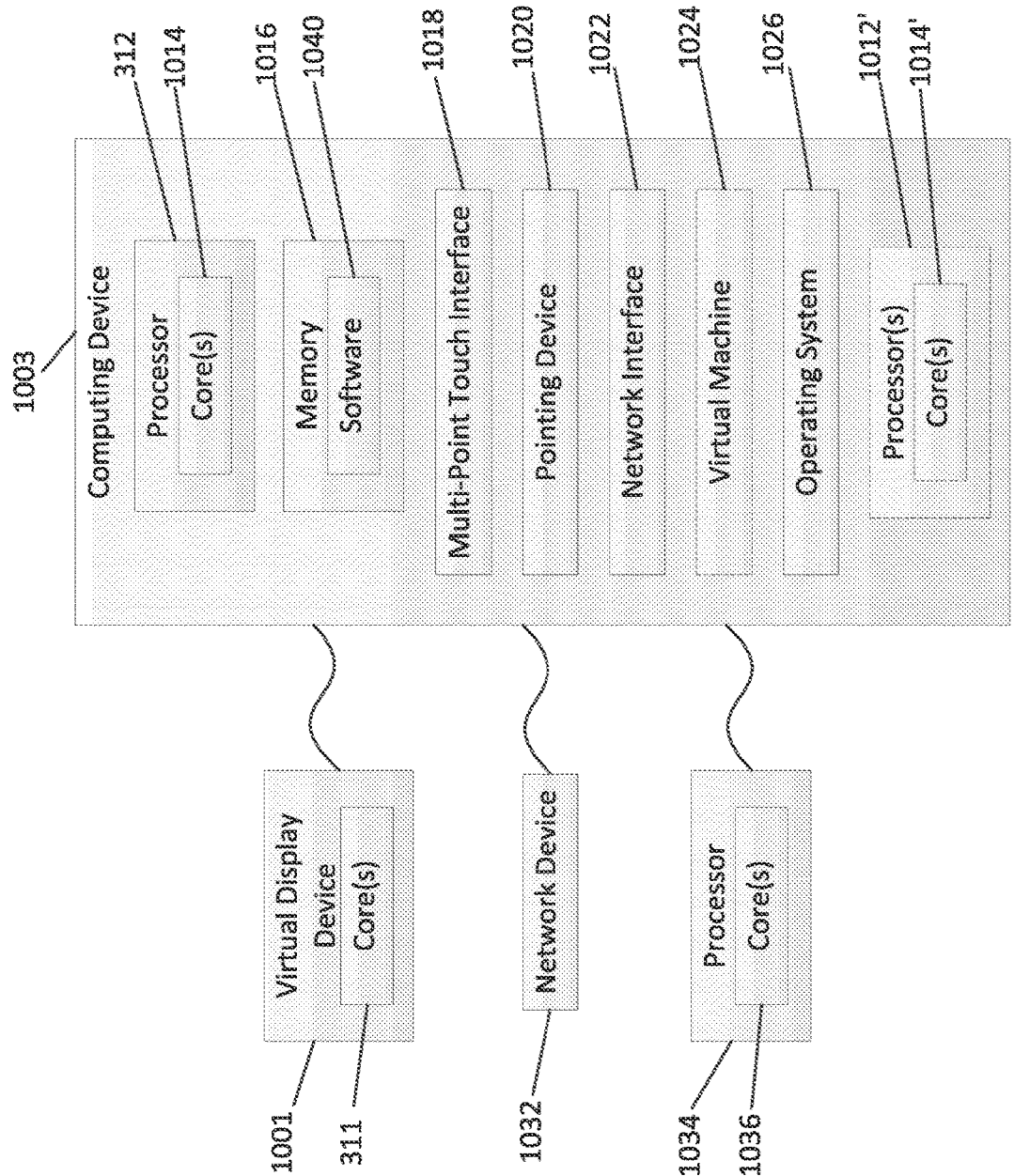
FIG. 6 is an exemplary computational device block diagram depicting various components that can be used to implement various of the disclosed embodiments.

FIG. 6 is a block diagram of an exemplary computing device 1010 such as can be used, or portions thereof, in accordance with various embodiments as described above with reference to FIGS. 1-5. The computing device 1010 includes one or more non-transitory computer-readable media for storing one or more computer-executable instructions or software for implementing exemplary embodiments. The non-transitory computer-readable media can include, but are not limited to, one or more types of hardware memory, non-transitory tangible media (for example, one or more magnetic storage disks, one or more optical disks, one or more flash drives), and the like. For example, memory 1016 included in the computing device 1010 can store computer-readable and computer-executable instructions or software for performing the operations disclosed herein. For example, the memory can store software application 1040 which is programmed to perform various of the disclosed operations as discussed with respect to FIGS. 1-5. The computing device 1010 can also include configurable and/or programmable processor 1012 and associated core 1014, and optionally, one or more additional configurable and/or programmable processing devices, e.g., processor(s) 1012' and associated core(s) 1014' (for example, in the case of computational devices having multiple processors/cores), for executing computer-readable and computer-executable instructions or software stored in the memory 1016 and other programs for controlling system hardware. Processor 1012 and processor(s) 1012' can each be a single core processor or multiple core (1014 and 1014') processor.

Virtualization can be employed in the computing device 1010 so that infrastructure and resources in the computing device can be shared dynamically. A virtual machine 1024 can be provided to handle a process running on multiple processors so that the process appears to be using only one computing resource rather than multiple computing resources. Multiple virtual machines can also be used with one processor.

Memory 1016 can include a computational device memory or random access memory, such as but not limited to DRAM, SRAM, EDO RAM, and the like. Memory 1016 can include other types of memory as well, or combinations thereof.

A user can interact with the computing device 1010 through a visual display device 101, 111A-D, such as a computer monitor, which can display one or more user interfaces 102 that can be provided in accordance with exemplary embodiments. The computing device 1010 can include other I/O devices for receiving input from a user, for example, a keyboard or any suitable multi-point touch interface 1018, a pointing device 1020 (e.g., a mouse). The keyboard 1018 and the pointing device 1020 can be coupled to the visual display device 101, 111A-D. The computing device 1010 can include other suitable conventional I/O peripherals.

The computing device 1010 can also include one or more storage devices 1034, such as but not limited to a hard-drive, CD-ROM, or other computer readable media, for storing data and computer-readable instructions and/or software that perform operations disclosed herein. Exemplary storage device 1034 can also store one or more databases for storing any suitable information required to implement exemplary embodiments. The databases can be updated manually or automatically at any suitable time to add, delete, and/or update one or more items in the databases.

The computing device 1010 can include a network interface 1022 configured to interface via one or more network devices 1032 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 1022 can include a built-in network adapter, network interface card, PCMCIA network card, card bus network adapter, wireless network adapter, USB network adapter, modem or any other device suitable for interfacing the computing device 1010 to any type of network capable of communication and performing the operations described herein. Moreover, the computing device 1010 can be any computational device, such as a workstation, desktop computer, server, laptop, handheld computer, tablet computer, or other form of computing or telecommunications device that is capable of communication and that has sufficient processor power and memory capacity to perform the operations described herein.

The computing device 1010 can run any operating system 1026, such as any of the versions of the Microsoft® Windows® operating systems (Microsoft, Redmond, Wash.), the different releases of the Unix and Linux operating systems, any version of the MAC OS® (Apple, Inc., Cupertino, Calif.) operating system for Macintosh computers, any embedded operating system, any real-time operating system, any open source operating system, any proprietary operating system, or any other operating system capable of running on the computing device and performing the operations described herein. In exemplary embodiments, the operating system 1026 can be run in native mode or emulated mode. In an exemplary embodiment, the operating system 1026 can be run on one or more cloud machine instances.

Figure 7:
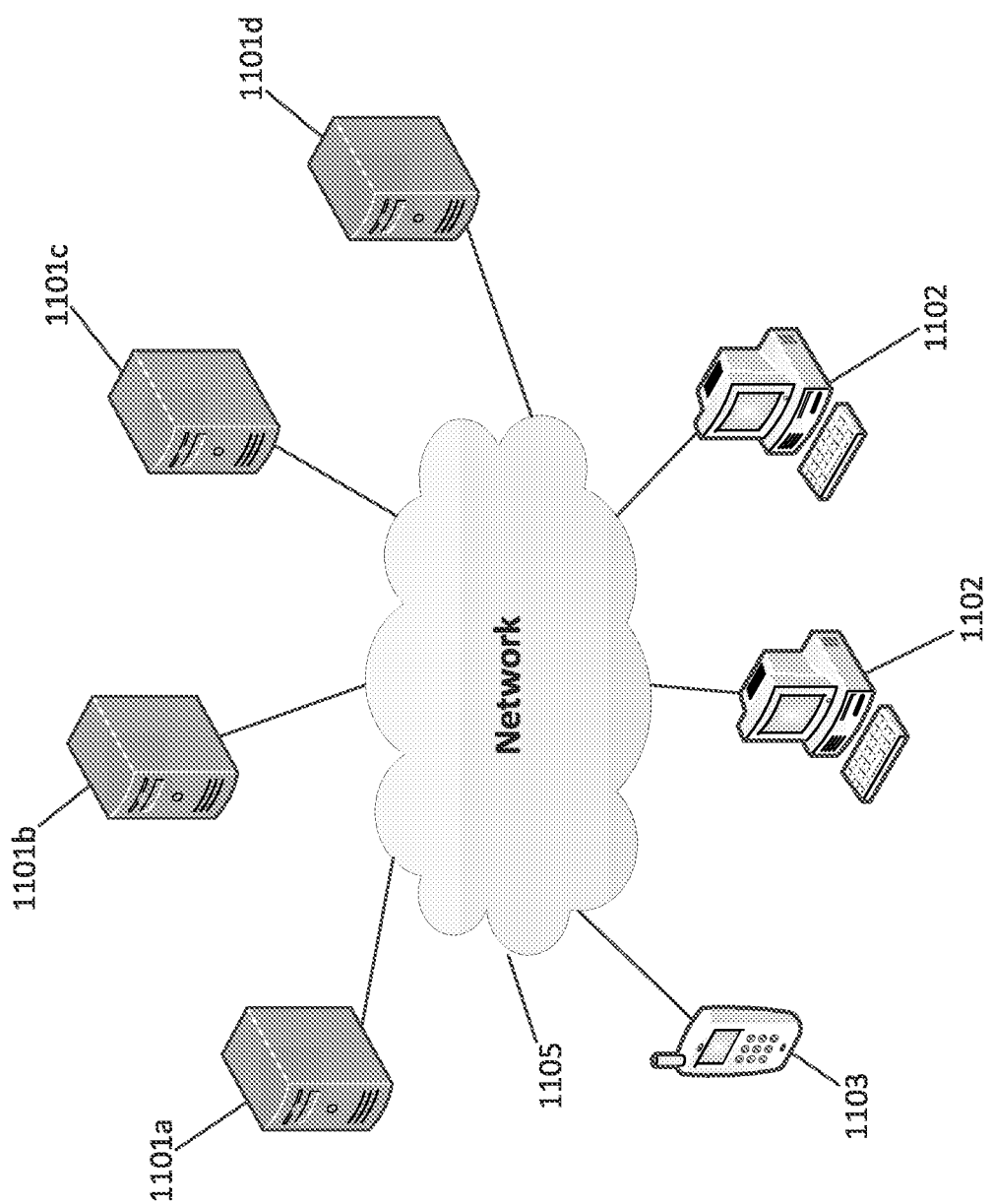
FIG. 7 is an exemplary computational device block diagram depicting various components that can be used to implement various of the disclosed embodiments in a distributed system.

FIG. 7 is an example computational device block diagram of certain distributed embodiments. Although FIGS. 1 and 6, and portions of the exemplary discussion above, make reference to a centralized multi-display system 100 operating on a single computing device, one will recognize that various of the modules within the multi-display system 100 may instead be distributed across a network 1105 in separate server systems 1101*a-d* and possibly in user systems, such as kiosk, desktop computer device 1102, or mobile computer device 1103. For example, users may download an application to their desktop computer device or mobile computer device, which is configured to show an interactive digital rendering of the meeting room and perform the operations of the display device 101, graphical user interface 102, output modules 109A-D, and/or output displays 111A-D. In some distributed systems, the modules of the multi-display system 100 can be separately located on server systems 1101*a-d* and can be in communication with one another across the network 1105.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

The invention claimed is:

1. A beam splitting apparatus comprising:
   a cylindrical housing defining an interior volume and having a first surface at a first end of the housing, a second surface at a second end of the housing, the second surface parallel to the first surface, and a third surface perpendicular to and extending between the first surface and the second surface, and
   an inlet defined in the first surface of the housing and defining an optical input path for receiving an optical input;
   a beam splitter positioned within the interior volume and optically coupled to the inlet for receiving the optical input, the beam splitter configured to split the optical input into a first optical output and a second optical output;
   a first outlet, defined in the second surface of the housing and defining a first optical output path for emitting the first optical output; and
   a second outlet, defined in the third surface of the housing and defining a second optical output path for emitting the second optical output.

2. The beam splitting apparatus of claim 1 wherein the beam splitter is further configured to split the optical input into a third optical output, the beam splitting apparatus further comprising:
   a third outlet, defined in at least one of the second surface or the third surface of the housing and defining a third optical output path for emitting the third optical output.

3. The beam splitting apparatus of claim 2 wherein the beam splitter is further configured to split the optical input into at least one additional optical output, the beam splitting apparatus further comprising:
   at least one additional outlet, defined in the housing and defining at least one additional optical output path for emitting the at least one additional optical output.

4. The beam splitting apparatus of claim 1, wherein the beam splitter is at least one of a polarizing beam splitter, non-polarizing beam splitter, Wollaston prism, pellicle beam splitter, dichroic beam splitter, mirror-type beam splitter, plate beam splitter, cube beam splitter, polka dot beam splitter, Brewster window, variable beam splitter, or wedged beam splitter.

5. A microscope retrofitting kit for a microscope having an objective lens and an eyepiece comprising:

a beam splitting apparatus removably attachable to the microscope between the objective lens and the eyepiece including:
- an inlet portion optically coupleable to the objective lens for forming an optical input path between the inlet and the objective lens for communicating an optical input,
- a beam splitter optically coupled to the inlet for receiving the optical input, the beam splitter configured to split the optical input into a first optical output and a second optical output,
- a first outlet, optically coupleable to the eyepiece for forming a first optical output path between the beamsplitter and the eyepiece for communicating the first optical output, and
- a second outlet, optically coupled to an image sensor for forming a second optical output path between the beamsplitter and the image sensor for communicating the second optical output; and
the image sensor optically coupled to the second outlet for receiving the second optical output, the image sensor configured to acquire image data from the second optical output.

6. The microscope retrofitting kit of claim 5, further comprising a display device in electrical communication with the image sensor, the display device configured to display an acquired image representing the image data acquired by the image sensor.

7. The microscope retrofitting kit of claim 5, wherein the eyepiece is a binocular eyepiece and the beam splitter is further configured to split the optical input into a third optical output, the beam splitting apparatus further comprising:
- a third outlet, optically coupleable to the eyepiece for forming a third optical output path between the beamsplitter and the eyepiece for communicating the third optical output.

8. The microscope retrofitting kit of claim 6, wherein the beam splitter is further configured to split the optical input into an additional optical output, the beam splitting apparatus further comprising:
- an additional outlet, optically coupled to a second image sensor for forming an optical output path between the beamsplitter and the second image sensor for communicating the additional optical output;
- the second image sensor optically coupled to the additional outlet for receiving the additional optical output, the second image sensor configured to acquire additional image data from the additional optical output; and
- a second display device in electrical communication with the second image sensor, the second display device configured to display a second acquired image representing the additional image data acquired by the second image sensor.

9. The microscope retrofitting kit of claim 6, further comprising a processing device configured to:
- receive surgical instrument operation data from one or more surgical instruments; and
- instruct at least one of the display device or an additional display device to display the received surgical instrument operation data.

10. The microscope retrofitting kit of claim 6, further comprising a processing device configured to:
- receive patient data from at least one of a patient data store or a patient monitoring system, and
- instruct at least one of the display device or the additional display device to display the received patient data.

11. The microscope retrofitting kit of claim 6, further comprising a processing device configured to:
- receive the acquired image data; and
- instruct the display device to display the acquired image representing the acquired image data.

* * * * *